(12) United States Patent
McArthur (10) Patent No.: US 10,627,385 B2
(45) Date of Patent: Apr. 21, 2020

(54) METHOD AND APPARATUS FOR INVESTIGATING FRAGMENT FIELDS CAUSED BY AN EXPLOSION

(71) Applicant: Thornton Tomasetti, Inc., New York, NY (US)

(72) Inventor: Chad McArthur, New York, NY (US)

(73) Assignee: THORNTON TOMASETTI, INC., New York, NY (US)

(*) Notice: Subject to any disclaimer, the term of this patent is extended or adjusted under 35 U.S.C. 154(b) by 407 days.

(21) Appl. No.: 15/480,205

(22) Filed: Apr. 5, 2017

(65) Prior Publication Data

US 2017/0284992 A1    Oct. 5, 2017

Related U.S. Application Data

(60) Provisional application No. 62/318,552, filed on Apr. 5, 2016.

(51) Int. Cl.
| | | |
|---|---|---|
| *G01N 33/22* | (2006.01) | |
| *G01P 3/36* | (2006.01) | |
| *G01G 9/00* | (2006.01) | |
| *G01P 3/12* | (2006.01) | |

(52) U.S. Cl.
CPC .......... *G01N 33/227* (2013.01); *G01G 9/00* (2013.01); *G01P 3/12* (2013.01); *G01P 3/36* (2013.01)

(58) Field of Classification Search
CPC .................................................. G01N 33/227
See application file for complete search history.

(56) References Cited

U.S. PATENT DOCUMENTS

| | | | | |
|---|---|---|---|---|
| 3,379,974 A | * | 4/1968 | Dryden | B64G 1/66 324/180 |
| 2012/0228507 A1 | * | 9/2012 | Rahman | B82Y 20/00 250/339.11 |
| 2014/0153772 A1 | * | 6/2014 | Guymon | G06K 9/78 382/103 |

FOREIGN PATENT DOCUMENTS

RU    2627346 C1 * 8/2017

* cited by examiner

*Primary Examiner* — Luke D Ratcliffe
(74) *Attorney, Agent, or Firm* — Arent Fox LLP (57) ABSTRACT

The present disclosure relates to methods and devices for investigating and characterizing a fragment or debris field caused by an explosion, and in particular, explosions resulting from the detonation of a cased munition. Aspects of the disclosure provide methods and devices which can be used to determine and correlate properties such as size/mass, location and velocity of fragments resulting from such a detonation.

20 Claims, 6 Drawing Sheets

METHOD AND APPARATUS FOR INVESTIGATING FRAGMENT FIELDS CAUSED BY AN EXPLOSION

CROSS-REFERENCE TO RELATED APPLICATION

This application claims priority to U.S. Provisional Patent Application No. 62/318,552, filed Apr. 5, 2016, the content of which is incorporated herein by reference in its entirety.

GOVERNMENT RIGHTS

This invention was made with government support under Contract No. DTRA2-11-D-0001 awarded by the U.S. Defense Threat Reduction Agency. The government has certain rights in the invention.

TECHNICAL FIELD

The present disclosure relates to methods and devices for investigating and characterizing a fragment or debris field caused by an explosion, and in particular, explosions resulting from the detonation of a cased munition. Aspects of the disclosure provide methods and devices which can be used to determine and correlate properties such as size/mass, location and velocity of fragments resulting from such a detonation.

BACKGROUND

Ballistic pendulums have been used since the early days of applying the scientific method to the study of ballistics to determine the speed and momentum of bullets and other projectiles. More recently, attempts to understand the fragmentation of a cased munition upon its detonation have used high speed digital video cameras and following the trial, recovery of the fragments to weigh them and calculate the kinetic energy of the fragments. Other investigators have measured pressure waves in the vicinity of a detonation. There is, however, a need for a more robust system capable of use in extreme loading environments

BRIEF SUMMARY OF EXEMPLARY ASPECTS

The present disclosure provides various configurations of a system for measurement of fragment characteristics and related methods which reduce or eliminates the above-identified problems in the art. In addition, selected aspects of the disclosure provide other benefits and solutions as discussed in detail below.

In a first exemplary aspect, a system for determining fragment characteristics according to the present disclosure comprises a culvert having a front aperture and a chute portion, a pendulum hung from at least two pivot points in said culvert, said pendulum having a strike face having a plurality of attachment points on which at least one witness panel may be mounted; at least one witness panel mounted on said pendulum; one or more leaf springs mounted on the back of the pendulum and configured to limit the motion of the pendulum when impacted by fragments resulting from an explosion; and at least one high speed camera mounted within said culvert.

In select aspects, the camera is a video camera capable of recording video at a frame rate of at least 3,000 frames per second.

In select aspects, the system further comprises a sensor mounted on the pendulum or the witness panel, wherein the sensor is configured to determine a parameter of fragments which impact the pendulum.

In select aspects, the system further comprises a plurality of high-speed cameras mounted within the culvert.

In select aspects, the plurality of high-speed cameras are configured to trigger at times offset from each other.

In select aspects, the leaf springs comprise stacked high-strength steel plates adapted to provide resistance to the motion of the pendulum.

In select aspects, the witness panel mounted on the pendulum is a crushable type of panel.

In select aspects, the pendulum further comprises one or more through-hole mounting points adapted to anchor face-mounted instruments (e.g., a pressure gauge).

In select aspects, the system further comprises a computer configured to communicate with the at least one high-speed camera mounted within the culvert; measure the movement of the pendulum following the impact of one or more fragments resulting from an explosion, based on photos or video received from the at least one high-speed camera; and determine characteristics of the one or more fragments, based on the movement of the pendulum.

In select aspects, the characteristics of the one or more fragments include one or more of the following: a mass, a location or a velocity.

In another exemplary aspect, method for determining fragment characteristics, comprising: (a) providing a culvert comprising: (i) a front aperture and a chute portion; (ii) a pendulum hung from at least two pivot points in the culvert, the pendulum comprising a strike face which has a plurality of attachment points upon which at least one witness panel may be mounted; (iii) at least one witness panel mounted on the pendulum; (iv) one or more leaf springs mounted on the back of the pendulum and configured to limit the motion of the pendulum when impacted by fragments resulting from an explosion; and (v) at least one high-speed camera mounted within the culvert; (b) orienting the aperture of the culvert towards an explosion; (c) measuring the movement of the pendulum and recording the movement of one or more fragments generated by the explosion within the culvert using at least one high-speed camera; and (d) determining characteristics of the one or more fragments, based on the movement of the pendulum.

In select aspects, the method may be performed using a system according to any of the various exemplary aspects disclosed herein.

In another exemplary aspect, the disclosure provides a method for determining fragment characteristics resulting from an explosion, for example of a cased munition, which comprises orienting the aperture of the culvert towards an explosion and then measuring the movement of the pendulum and recording the movement of fragments generated by the explosion within the culvert by use of one or more high speed video cameras.

In some exemplary aspects, the culvert is configured to determine fragment characteristics resulting from an explosion originating along a lateral axis, However, it is understood that any of the systems and methods disclosed herein may also be used to determine fragment characteristics resulting from an explosion originating below the pendulum (e.g., a landmine). In such aspects, the culvert and any other structural elements described herein may be adjusted or reoriented to account for the change in position of the source of the explosion. Similarly, the algorithms described below may be readily modified as needed to account for the new orientation (e.g., by adjusting gravity-related or other parameters).

This simplified summary of exemplary aspects of the disclosure serves to provide a basic understanding of the invention. This summary is not an extensive overview of all contemplated aspects, and is intended to neither identify key or critical elements of all aspects nor delineate the scope of any or all aspects of the invention. Its sole purpose is to present one or more aspects in a simplified form as a prelude to the more detailed description of the invention that follows. To the accomplishment of the foregoing, the one or more aspects of the invention include the features described and particularly pointed out in the claims.

DETAILED DESCRIPTION OF EXEMPLARY ASPECTS

Exemplary aspects of the disclosure are described herein in the context of a system and method for determining fragment characteristics, various aspects of which being suitable for measuring fragment characteristics of explosives and ordinance.

As indicated above, in select aspects, systems and methods according to the disclosure may use a culvert structure to contain the explosion or blast being characterized. The culvert performs a number of important functions in that it:
1. Provides support and mounting points for the pendulum and leaf springs.
2. Provides mounting and handling point used to move, re-configure, and mount the entire module as part of larger measurement array;
3. Provides at least one aperture for "sampling" a discrete region from the broader, more chaotic, global fragment field;
4. Provides a protected environment within the debris field to mount camera and lighting arrangements;
5. Provides a defined volume as an optical environment (camera box) to simplify control of focal lengths, background contrast, and lighting environment; and
6. Provides support and mounting points for various instrumentation package configurations.

The pendulum used by the disclosed systems and methods differs from a classical ballistic pendulum. For example, in many exemplary aspects it is hung from two pivot points so that the pendulum moves the same amount regardless of where fragments impact the target face of the pendulum. The bob of the pendulum should typically be of a sufficient mass that its movement can be measured, but not of such a mass that its movement can cause damage to other parts of the structure. In some exemplary aspects, the bob is supported by two pivot arms affixed to the upper inner surface of the culvert. Furthermore, in some exemplary aspects the pendulum may be a concrete-filled, fabricated steel box in order to achieve high mass and high impact resistance. The front face of the pendulum may be configured to include attachment points around the perimeter to facilitate installation of different strike-face materials or witness panels.

In some exemplary aspects, the pendulum may also provide one or more through-hole mounting points so that face-mounted instrumentation (e.g. reflected pressure gages) can be installed, and the cabling drawn through the body of the pendulum and not exposed to the severe fragment environment. In operation, the motion of the pendulum caused by impact of fragments on the witness panel provides a time-dependent record of the amount, severity, and timing of fragment impacts on the face of the pendulum. The pendulum featured in the disclosed methods and systems provides a measurement of the amount of impulse imparted to the pendulum (e.g., by fragments and air blast) over time. As a result, the pendulum-based configuration represents a significant advancement over current arena testing methodologies because it provides the ability for one to quantify the mass, location, and velocity of fragments per area, over the face of the pendulum.

As indicated above, in some aspects the primary function of the culvert is to provide support for hanging the pendulum. It may also provide attachment points for anchoring the assembly to a ground slab and also for attaching other adjacent assemblies together to offer a larger array of measurement area. The culvert also provides a "chute" down which fragments have to travel prior to hitting the witness panel. This chute offers an environment that can be used to control the optical environment (e.g. lighting, contrast, etc.) needed for high-quality video recording.

The witness panel mounted on the pendulum is typically a "crushable" type of panel (e.g. Celotex® or other foam-board bundles, or aluminum foam or honeycomb panels), which may be used so that the fragments get "trapped" in the bundle, preventing potential ricochets. This configuration also allows for post-test forensics to be performed by "picking" fragments from the bundle to gather additional data on the exact size and location of the fragments.

Figure 1:
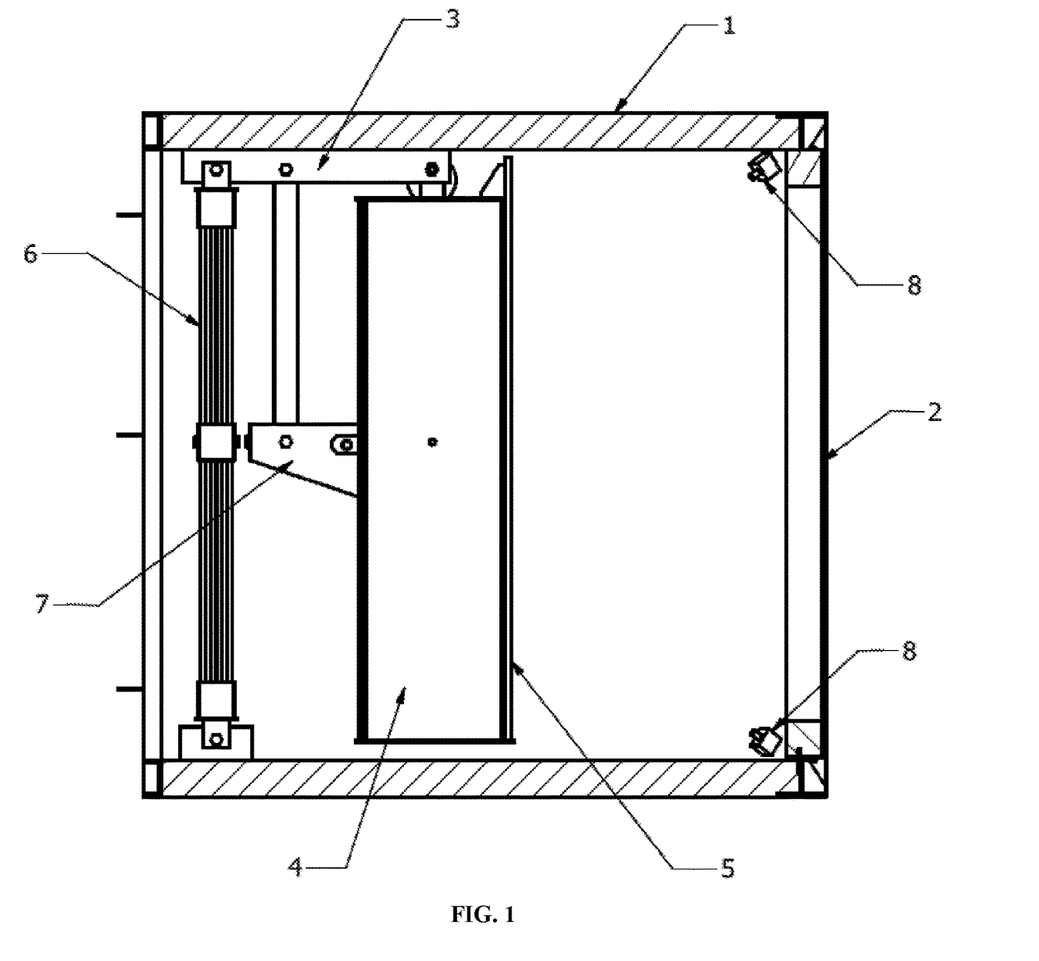
FIG. 1 is a schematic longitudinal section view of a system according to an exemplary aspect of the present disclosure.
Figure 2:
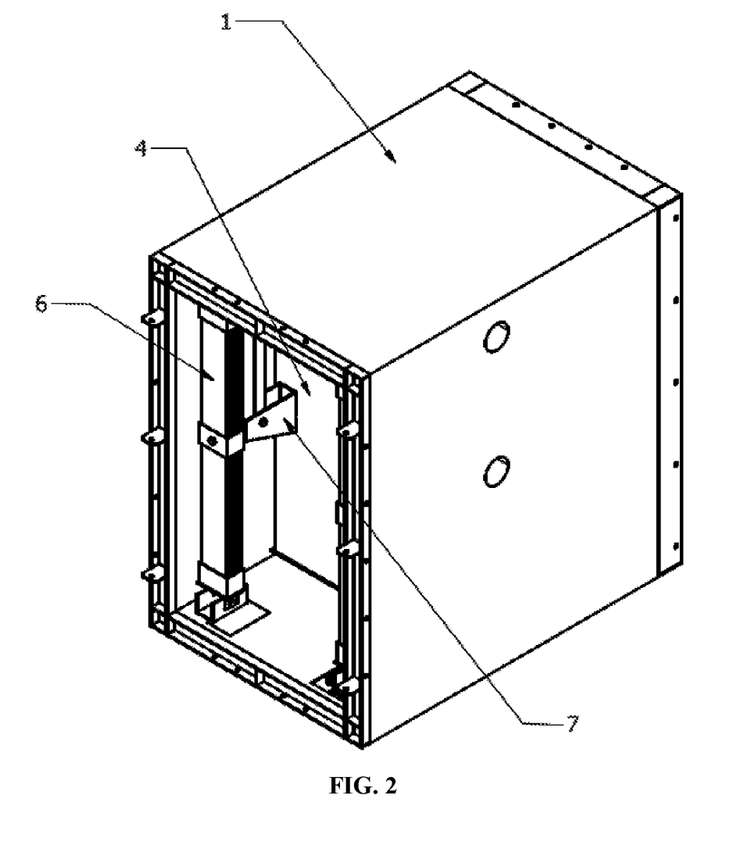
FIG. 2 is an isometric view of the rear part of the system shown in FIG. 1, which illustrates the mounting of the leaf springs and their connection to the pendulum.
Figure 3A:
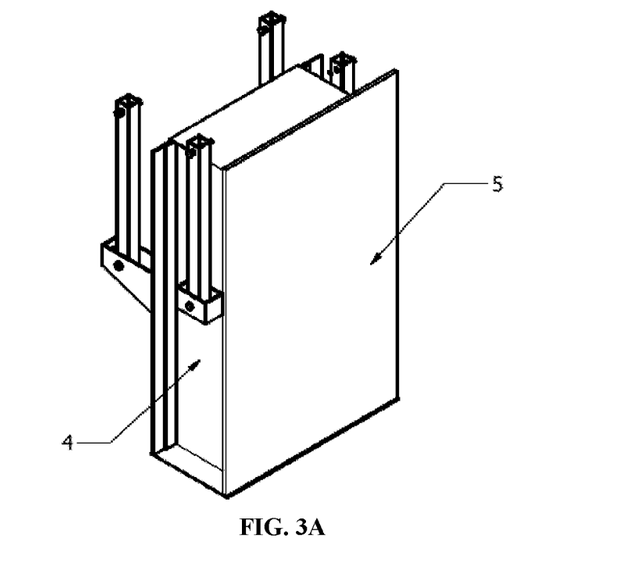
FIG. 3A is a front isometric view of the system shown in FIG. 1.
Figure 3B:
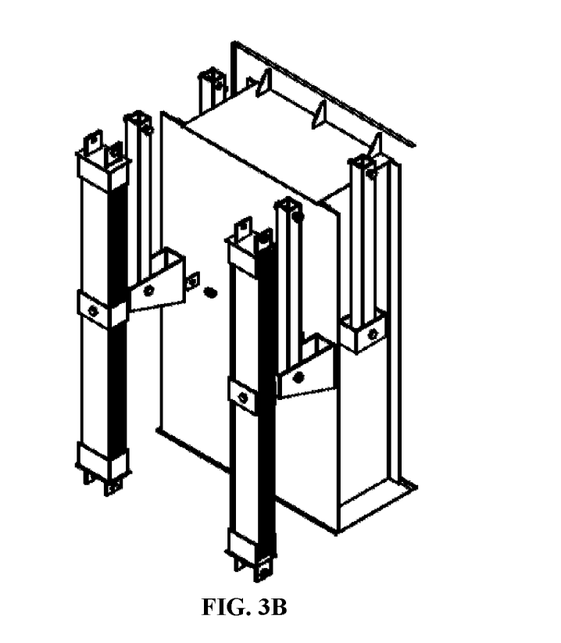
FIG. 3B is a rear isometric view of a pendulum assembly which may be used in select aspects of the present disclosure.
Figure 4:
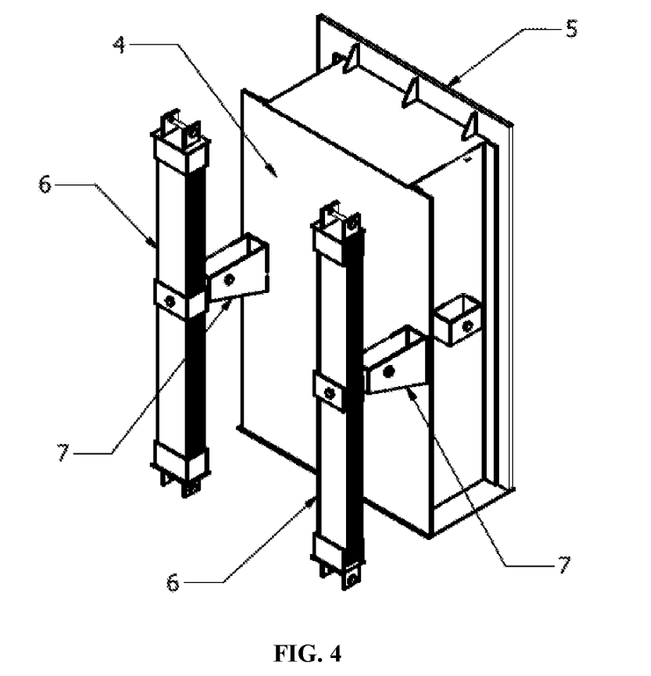
FIG. 4 is a rear isometric view of a leaf spring assembly as connected to back of a pendulum assembly showing leaf springs mounted on the back of the pendulum (e.g., to limit the motion of the pendulum when impacted by fragments resulting from an explosion).

In some exemplary aspects, the leaf springs may comprise stacked high-strength steel plates which provide additional resistance to the motion of the pendulum. These plates may be mounted to the back of the pendulum as shown in FIG. 4, wherein they may be anchored top and bottom to the culvert, though this particular configuration was omitted from FIG. 4 for clarity. For severe loading environments encountered during the proposed tests, it is generally impractical to field a pendulum that is heavy enough to prevent excessive motion when resisted solely by gravity. As a result, the high-stiffness/high-deformation leaf springs described herein are implemented to control the motion of the pendulum and to limit the deformation during the test to just a few inches. The resistance and allowable deformation of the leaf springs may be controlled by varying the number and thickness of plates used. If necessary, friction between the leaf spring plates may be controlled by polish/waxing the contact surface and/or interleaving thin sheets of high density polyethylene (e.g., Teflon®) to control and maintain reliable operation of the leaf springs. In some exemplary aspects, the leaf springs may be connected to the pendulum bob with bolts that can be tightened to remove any initial play or "slop" in the connected assemblies and ensure prompt response of the system.

High-speed cameras for use with the present systems and methods may be selected based upon the size and velocity range of fragments to be recorded. Any camera that is able to provide photos or videos sufficient to allow one to identify the time at which specific fragments impact the witness panel will typically be suitable for the present methods and systems. Using this timing parameter, one can then estimate the velocity at which any given fragments was traveling (based on the distance from the source). For example, a system sufficient to track fragment sizes down to 2 mm at speeds up to 8,000 frames per second (fps) would require resolution no less than 720p and frame rates up to 3,000 fps or more to identify the velocity within an accuracy of 5% at a 45 foot range.

These specifications can be achieved with a single high-speed camera in some exemplary aspects (e.g., a Phantom® Miro C210) or, alternatively, with several slower cameras configured to trigger at times offset from each other to provide the appropriate aggregate frame rate. Furthermore, in some aspects multiple very high-speed, high-resolution cameras may be used to video the fragments from several different angles as they travel through the culvert and the fragment size, position, and velocity may be determined through the use of various motion-tracking video analysis algorithms. Other measurement equipment such as pressure gauges may also be mounted on the pendulum or the witness panel.

The systems and methods of the present disclosure enable characterization of correlated properties (size/mass, location, and velocity of individual fragments generated by an explosion such as the detonation of a cased munition. In some exemplary aspects, when placed directly in the range of the fragment or debris field, the combined measurement assembly may be configured to gather all of the essential data necessary to characterize the portion of the fragment field that enters through a front aperture of the culvert. In some exemplary aspects (e.g., as illustrated by the provided figures), fragments travel through the "chute" portion of the culvert prior to impacting the witness panel on the front strike-face of the pendulum. In operation, the motion of the pendulum caused by impact of fragments on the witness panel provides a time-dependent record of the amount, severity, and timing of fragment impacts on the face of the pendulum. The time at which the fragments impact the witness panel on the front face of the pendulum may be recorded optically by high speed cameras, which are mounted within the culvert. In some exemplary aspects, the camera will be mounted in a protected space, such as behind a panel or within an enclosure.

As described above, systems and methods according to the disclosure may be used to quantify the mass, location, and velocity of fragments per area, over the face of the pendulum. The mathematical relations to do this are straightforward so it is simple to describe them here:

Impulse=momentum/area; and

Momentum=mass×($V_1$-$V_2$).

Since fragment velocity does not change dramatically from the time of the explosion or case-break-up to impact, $V_1$=Distance/TOA (where "TOA" is the time at which the fragment hits the witness panel). $V_2$ is a function of $V_1$ and the coefficient of restitution ("COR"). If a crushable witness panel is used to arrest the fragments, then COR=1 and $V_2$=0.

Therefore, Impulse=(mass×distance/TOA/area). Based on this scaling, the pendulum is actually measuring fragment mass per area over time, and the time corresponds to the velocity of fragments. Furthermore, if more information is required, fragments may be extracted out of the witness panel to correlate fragment size with position.

As noted above, the data obtained by the video cameras may be analyzed algorithmically. The approach for doing this is straightforward and outlined here for any single object:

Two (or more) photographs of an object are taken from two different (known) locations and orientations.

The size and position of the object is then determined by simple trigonometry if you know the camera's lens focal length, and sensor (film) size.

These steps are repeated at a later time to determine how much the object has moved and thereby estimate the velocity of the object.

This algorithm lends itself to various programmable approaches such that a computer can perform the necessary manipulations for numerous fragments over numerous frames of video.

However, doing this on a large scale presents numerous challenges. In order to be able to estimate fragment speed, an individual fragment has to be specifically identified from one frame to the next. In a crowded fragment field, the most reliable way to do this is if the relative movement from one frame to the next is relatively small. For fragments moving at 6,000 to 8,000 ft/sec, a minimum frame-rate of 10,000 to 20,000 fps, (possibly higher) is needed to track the position (velocity) of individual fragments.

Even when placed outside the fragment field, the cameras may still be in a severe environment and are likely to move to some degree as a result of the air blast shock load. Cameras should be shock-isolated and/or any changes in their position/orientation should be recorded so that the motion can be subtracted-out of fragment position/velocity calculations.

One way to mitigate these challenges positions cameras in a protected space within the debris field for example by extending the culvert to form a "chute" in front of the pendulum and flange/chamfer in the aperture to create a protected space to house lighting and small form-factor cameras. In this scenario, the optical environment (lighting and background contrast) can be controlled, and there are fewer fragments within the field of view to attempt to identify and track.

Furthermore, optical measurements could be verified against measurements taken by the pendulum at the end of the chute.

With the proposed configuration, the speed of an individual specific fragment can also be determined based on the known distance between the point of the explosion and the witness panel and the time at which the fragment hits the witness panel (i.e., the TOA) because the speed of the fragment does not change substantially from the time of the explosion (for example when the weapon breaks up), to the time that it hits the front face to the witness panel. This can be achieved with a properly configured witness panel on the front face of the pendulum and a camera (or cameras) with a fast enough frame rate to determine TOA with reasonable accuracy pointed at the witness panel.

Additional benefits and aspects associated with the preceding description will be appreciated in view of the accompanying figures. FIGS. 1-4 illustrate an exemplary system according to the disclosure, which comprises a culvert (1) having an aperture (2) located at its front end. The culvert (1) contains a support frame (3), on which is mounted a pendulum (4), having a witness face (5) located on its front surface. Mounted within the culvert (1) behind the pendulum (4) is a leaf spring assembly (6) linked to the pendulum (4) by brackets (7). High speed cameras (8) angled to record impact on the witness plate are mounted within the culvert (1). The leaf spring assembly (6) extends from the top to the bottom of the culvert (1) and limit the rearwards motion of the pendulum (4) when its witness face is impacted by fragments of debris or an encased munition resulting from an explosion.

In operation, an explosion or detonation of an encased munition is caused to occur in front if the front aperture of the device. The distance at which the explosion occurs from the front of the device is predetermined and will vary according to the nature of the explosion under investigation. Debris or fragments from the explosion enter the culvert and impact the witness face of the pendulum and are embedded therein. The momentum of the impact causes the pendulum to be forced back against the leaf springs.

The mass of the pendulum used in the system and the force required to effect any given degree of movement against the leaf springs are understood to be known parameters determined prior to operation of the system. As a result, measurement of the movement of the pendulum can be used to calculate the kinetic energy resulting from the explosion impacting the witness plate. This information can be combined with that from the high speed cameras to obtain further information as to the distribution and kinetic energy of fragments resulting from the explosion or detonation.

Figure 5:
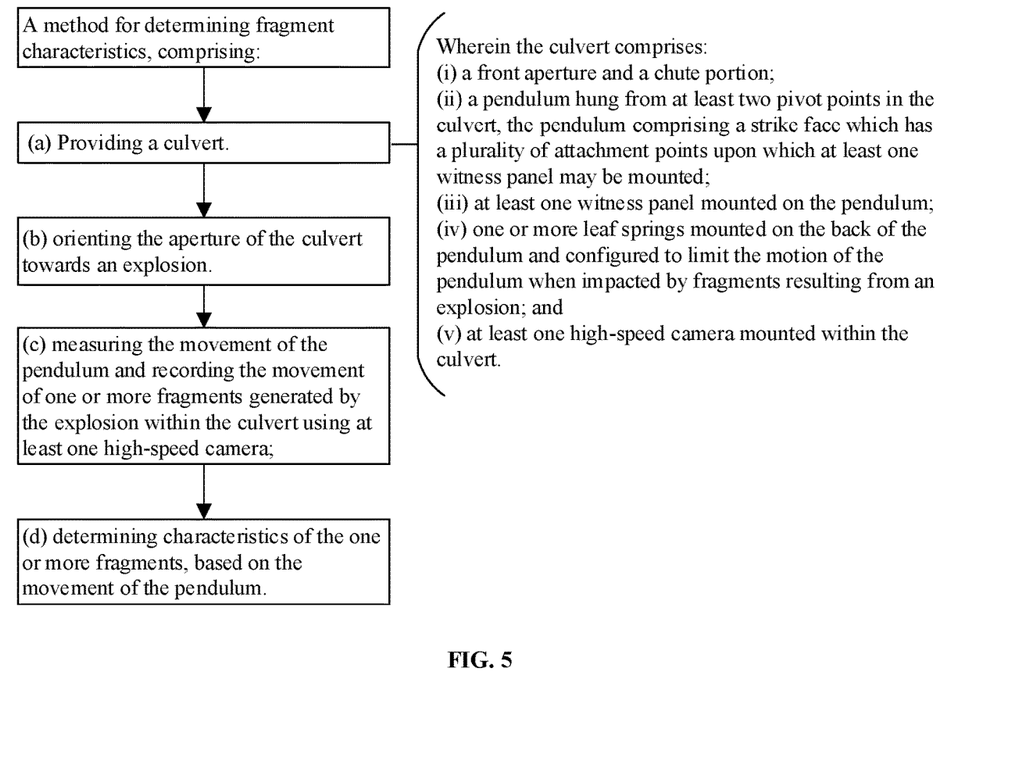
FIG. 5 is a block diagram that illustrates an exemplary method according to the present disclosure.

FIG. 5 is a block diagram that illustrates an exemplary method according to the present disclosure. As shown, a method for determining fragment characteristics according to the disclosure may include providing a culvert in accordance with any of the various exemplary aspects disclosed herein (e.g., using one or more photo or video camera, oriented to evaluate the fragment field of a horizontal or vertically-oriented blast, etc.). The culvert will typically include (i) a front aperture and a chute portion; (ii) a pendulum hung from at least two pivot points in the culvert, the pendulum comprising a strike face which has a plurality of attachment points upon which at least one witness panel may be mounted; (iii) at least one witness panel mounted on the pendulum; (iv) one or more leaf springs mounted on the back of the pendulum and configured to limit the motion of the pendulum when impacted by fragments resulting from an explosion; and (v) at least one high-speed camera mounted within the culvert. The aperture of the culvert may then be oriented towards an explosion, if it has not been oriented already. Upon triggering the explosion, one can measure the movement of the pendulum and record the movement of one or more fragments generated by the explosion within the culvert using at least one high-speed camera. In some alternative aspects, a plurality of high or low-speed cameras may be used (e.g., configured to trigger at times offset from each other). Finally, one may determine characteristics of the one or more fragments, based on the movement of the pendulum. In some exemplary aspects, additional data may be used to perform this determination (e.g., collected from one or more additional sensors placed on the pendulum or witness panel).

Figure 6:
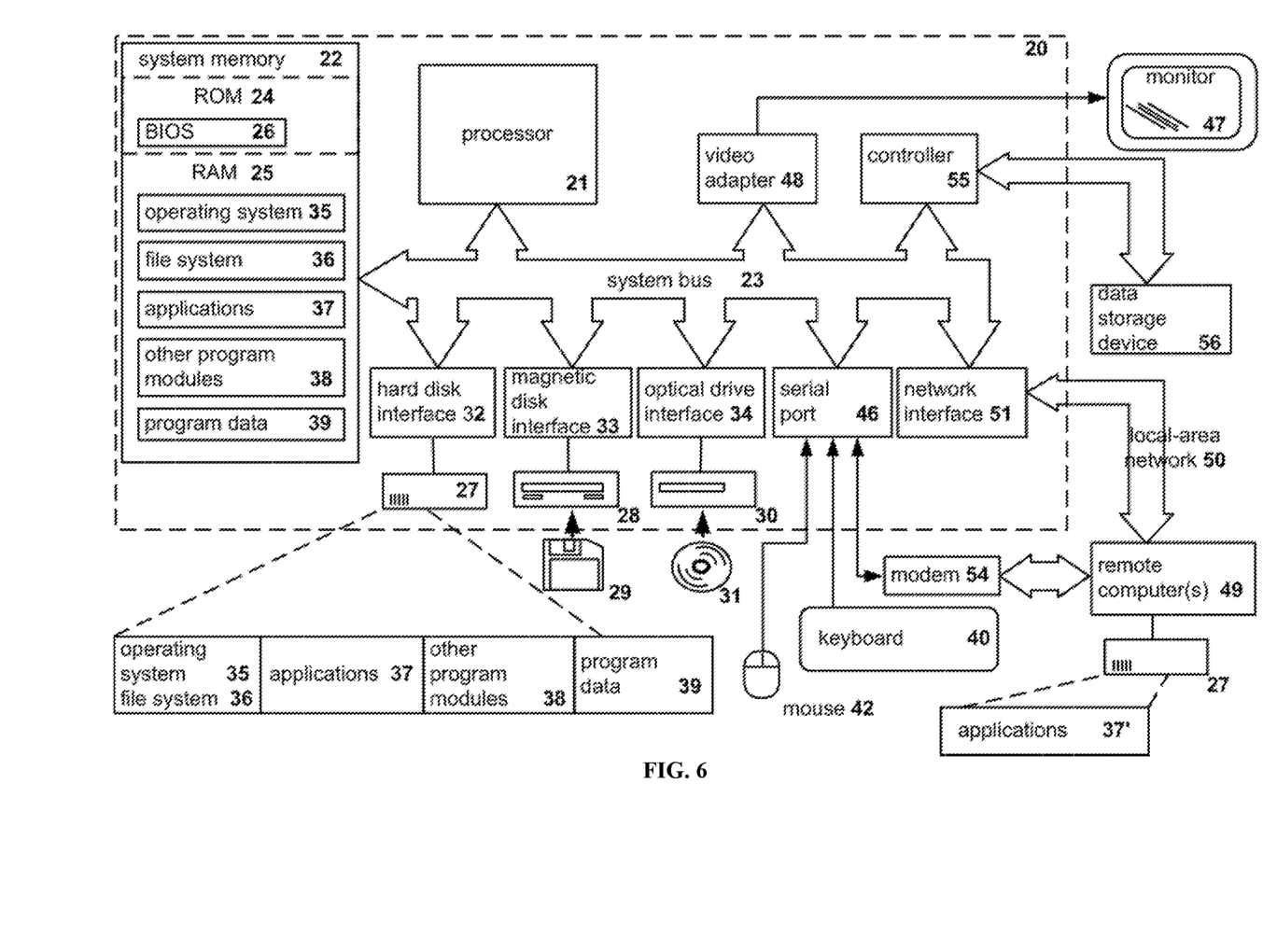
FIG. 6 illustrates an example of a general-purpose computer system (which may be a personal computer, server, or mobile device) which may be used to implement or automate aspects of the methods and systems disclosed herein.

FIG. 6 illustrates an example of a general-purpose computer system (which may be a personal computer or a server) on which the disclosed systems and method can be implemented according to some exemplary aspects. It should be appreciated that the detailed general-purpose computer system can correspond to the computer referenced above, which may be used to automate aspects of the methods disclosed herein.

As shown in FIG. 6, the computer system 20 includes a central processing unit 21, a system memory 22 and a system bus 23 connecting the various system components, including the memory associated with the central processing unit 21. The system bus 23 is realized like any bus structure known from the prior art, including in turn a bus memory or bus memory controller, a peripheral bus and a local bus, which is able to interact with any other bus architecture. The system memory includes read only memory (ROM) 24 and random-access memory (RAM) 25. The basic input/output system (BIOS) 26 includes the basic procedures ensuring the transfer of information between elements of the personal computer 20, such as those at the time of loading the operating system with the use of the ROM 24.

The personal computer 20, in turn, includes a hard disk 27 for reading and writing of data, a magnetic disk drive 28 for reading and writing on removable magnetic disks 29 and an optical drive 30 for reading and writing on removable optical disks 31, such as CD-ROM, DVD-ROM and other optical information media. The hard disk 27, the magnetic disk drive 28, and the optical drive 30 are connected to the system bus 23 across the hard disk interface 32, the magnetic disk interface 33 and the optical drive interface 34, respectively. The drives and the corresponding computer information media are power-independent modules for storage of computer instructions, data structures, program modules and other data of the personal computer 20.

The present disclosure provides the implementation of a system that uses a hard disk 27, a removable magnetic disk 29 and a removable optical disk 31, but it should be understood that it is possible to employ other types of computer information media 56 which are able to store data in a form readable by a computer (solid state drives, flash memory cards, digital disks, random-access memory (RAM) and so on), which are connected to the system bus 23 via the controller 55.

The computer 20 has a file system 36, where the recorded operating system 35 is kept, and also additional program applications 37, other program modules 38 and program data 39. The user is able to enter commands and information into the personal computer 20 by using input devices (keyboard 40, mouse 42). Other input devices (not shown) can be used: microphone, joystick, game controller, scanner, and so on. Such input devices usually plug into the computer system 20 through a serial port 46, which in turn is connected to the system bus, but they can be connected in other ways, for example, with the aid of a parallel port, a game port or a universal serial bus (USB). A monitor 47 or other type of display device is also connected to the system bus 23 across an interface, such as a video adapter 48. In addition to the monitor 47, the personal computer can be equipped with other peripheral output devices (not shown), such as loudspeakers, a printer, and so on.

The personal computer 20 is able to operate within a network environment, using a network connection to one or more remote computers 49. The remote computer (or computers) 49 are also personal computers or servers having the majority or all of the aforementioned elements in describing the nature of a personal computer 20, as shown in FIG. 6. Other devices can also be present in the computer network, such as routers, network stations, peer devices or other network nodes.

Network connections can form a local-area computer network (LAN) 50, such as a wired and/or wireless network, and a wide-area computer network (WAN). Such networks are used in corporate computer networks and internal company networks, and they generally have access to the Internet. In LAN or WAN networks, the personal computer 20 is connected to the local-area network 50 across a network adapter or network interface 51. When networks are used, the personal computer 20 can employ a modem 54 or other modules for providing communications with a wide-area computer network such as the Internet. The modem 54, which is an internal or external device, is connected to the system bus 23 by a serial port 46. It should be noted that the network connections are only examples and need not depict the exact configuration of the network, i.e., in reality there are other ways of establishing a connection of one computer to another by technical communication modules, such as Bluetooth.

In the interest of clarity not all of the routine features of the aspects are disclosed herein. It will be appreciated that in the development of any actual implementation of the present disclosure, numerous implementation-specific decisions must be made in order to achieve the developer's specific goals, and that these specific goals will vary for different implementations and different developers. It will be appreciated that such a development effort might be complex and time-consuming, but would nevertheless be a routine undertaking of engineering for those of ordinary skill in the art having the benefit of this disclosure.

Furthermore, it is to be understood that the phraseology or terminology used herein is for the purpose of description and not of restriction, such that the terminology or phraseology of the present specification is to be interpreted in light of the teachings and guidance presented herein, in combination with the knowledge available to a person of ordinary skill in the relevant art(s) at the time of invention. Moreover, it is not intended for any term in the specification or claims to be ascribed an uncommon or special meaning unless explicitly set forth as such in the specification.

The various aspects disclosed herein encompass present and future known equivalents to the known structural and functional elements referred to herein by way of illustration. Moreover, while aspects and applications have been shown and described, it would be apparent to those skilled in the art having the benefit of this disclosure that many more modifications than those mentioned above are possible without departing from the inventive concepts disclosed herein. For example, one of ordinary skill in the art would readily appreciate that individual features from any of the exemplary aspects disclosed herein may be combined to generate additional aspects that are in accordance with the inventive concepts disclosed herein.

Although illustrative exemplary aspects have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

The invention claimed is:

1. A system for determining fragment characteristics, comprising:
   a culvert having a front aperture and a chute portion;
   a pendulum hung from at least two pivot points in the culvert, the pendulum comprising a strike face which has a plurality of attachment points upon which at least one witness panel may be mounted;
   at least one witness panel mounted on the pendulum;
   one or more leaf springs mounted on the back of the pendulum and configured to limit the motion of the pendulum when impacted by fragments resulting from an explosion; and
   at least one high-speed camera mounted within the culvert.

2. The system for determining fragment characteristics of claim 1, wherein the high-speed camera is a video camera capable of recording video at a frame rate of at least 3,000 frames per second.

3. The system for determining fragment characteristics of claim 1, further comprising a sensor mounted on the pendulum or the witness panel, wherein the sensor is configured to determine a parameter of the fragments which impact the pendulum.

4. The system for determining fragment characteristics of claim 1, further comprising a plurality of high-speed cameras mounted within the culvert.

5. The system for determining fragment characteristics of claim 4, wherein the plurality of high-speed cameras are configured to trigger at times offset from each other.

6. The system for determining fragment characteristics of claim 1, wherein the leaf springs comprise stacked high-strength steel plates adapted to provide resistance to the motion of the pendulum.

7. The system for determining fragment characteristics of claim 1, wherein the witness panel mounted on the pendulum is a crushable type of panel.

8. The system for determining fragment characteristics of claim 1, wherein the pendulum further comprises one or more through-hole mounting points adapted to anchor face-mounted instruments.

9. The system for determining fragment characteristics of claim 1, wherein the system further comprises a computer configured to:
   communicate with the at least one high-speed camera mounted within the culvert;
   measure the movement of the pendulum following the impact of the one or more fragments resulting from an explosion, based on photos or video received from the at least one high-speed camera; and
   determine characteristics of the one or more fragments, based on the movement of the pendulum.

10. The system for determining fragment characteristics of claim 9, wherein the characteristics of the one or more fragments include one or more of the following: a mass, a location or a velocity.

11. A method for determining fragment characteristics, comprising:
    (a) providing a culvert comprising:
        (i) a front aperture and a chute portion;
        (ii) a pendulum hung from at least two pivot points in the culvert, the pendulum comprising a strike face which has a plurality of attachment points upon which at least one witness panel may be mounted;
        (iii) at least one witness panel mounted on the pendulum;

(iv) one or more leaf springs mounted on the back of the pendulum and configured to limit the motion of the pendulum when impacted by fragments resulting from an explosion; and (v) at least one high-speed camera mounted within the culvert;

(b) orienting the front aperture of the culvert towards an explosion;

(c) measuring the movement of the pendulum and recording the movement of the one or more fragments generated by the explosion within the culvert using at least one high-speed camera; and (d) determining characteristics of the one or more fragments, based on the movement of the pendulum.

12. The method for determining fragment characteristics of claim 11, wherein the at least one high-speed camera is a video camera capable of recording video at a frame rate of at least 3,000 frames per second.

13. The method for determining fragment characteristics of claim 11, further comprising determining a parameter of the fragments which impact the pendulum, using a sensor mounted on the pendulum or the witness panel.

14. The method for determining fragment characteristics of claim 11, further comprising mounting a plurality of high-speed cameras within the culvert.

15. The method for determining fragment characteristics of claim 14, wherein the plurality of high-speed cameras are configured to trigger at times offset from each other.

16. The method for determining fragment characteristics of claim 11, wherein the leaf springs comprise stacked high-strength steel plates adapted to provide resistance to the motion of the pendulum.

17. The method for determining fragment characteristics of claim 11, wherein the witness panel mounted on the pendulum is a crushable type of panel.

18. The method for determining fragment characteristics of claim 11, wherein the pendulum further comprises one or more through-hole mounting points adapted to anchor face-mounted instruments.

19. The method for determining fragment characteristics of claim 11, further comprising:

providing a computer configured to communicate with the at least one high-speed camera mounted within the culvert;

measuring, by the computer, the movement of the pendulum following the impact of one or more fragments resulting from an explosion, based on photos or video received from the at least one high-speed camera; and determining, by the computer, characteristics of the one or more fragments, based on the movement of the pendulum.

20. The method for determining fragment characteristics of claim 19, wherein the characteristics of the one or more fragments include one or more of the following: a mass, a location or a velocity.

* * * * *